United States Patent [19]
Ouchi et al.

[11] Patent Number: 6,077,274
[45] Date of Patent: Jun. 20, 2000

[54] BASKET-TYPE GRASPING TOOL ADAPTED FOR USE IN COMBINATION WITH AN ENDOSCOPE

[75] Inventors: Teruo Ouchi, Saitama; Miyuki Nishimura, Nagano, both of Japan

[73] Assignee: Asahi Kogaku Kogyo Kabushiki Kaisha, Tokyo, Japan

[21] Appl. No.: 09/148,876

[22] Filed: Sep. 8, 1998

[30]    Foreign Application Priority Data

Sep. 10, 1997   [JP]   Japan ........................................ 9-24490
Sep. 30, 1997   [JP]   Japan ........................................ 9-26570

[51] Int. Cl.⁷ .................................................. A61B 17/24
[52] U.S. Cl. ........................... 606/113; 606/127; 606/200
[58] Field of Search .................................. 606/127, 200, 606/108, 113, 110

[56]    References Cited
U.S. PATENT DOCUMENTS 4,046,150   9/1977   Schwartz et al. ........................ 606/127
4,347,846   9/1982   Dormia ..................................... 606/127
5,059,199   10/1991  Okada et al. ............................ 606/127

FOREIGN PATENT DOCUMENTS 53-14060   4/1978   Japan .
62-42617   9/1987   Japan .

Primary Examiner—Michael Buiz
Assistant Examiner—Kevin Truong
Attorney, Agent, or Firm—Greenblum & Bernstein, P.L.C.

[57]    ABSTRACT

A basket-type grasping tool, adapted for use in combination with an endoscope, for capturing a foreign material or the like into a basket section. Axially corresponding portions of elastic wires are each twisted in the same direction about a center axis of a basket section. Guide paths, through which the elastic wires respectively pass, are formed on an inner face of a tip-end mouth of a sheath.

15 Claims, 16 Drawing Sheets

BASKET-TYPE GRASPING TOOL ADAPTED FOR USE IN COMBINATION WITH AN ENDOSCOPE

BACKGROUND OF THE INVENTION

1. Field of the Invention

The present invention relates to a basket-type grasping tool adapted for use in combination with an endoscope to endoscopically capture a foreign material or the like within a body cavity and remove the same therefrom.

2. Description of the Related Art

In general, a basket-type grasping tool has a basket section formed by at least three elastic wires that are bundled at both front and rear ends. The basket section is contracted by retracting the basket section into the tip end of a sheath. When the basket section is extracted from the tip end of the sheath, the basket section is expanded into a basket-like shape by its own elasticity.

The basket-type grasping tool is used such that the basket section is reciprocated in the axial direction of the sheath with respect to a foreign material or the like on the mucosa surface within a body cavity to endoscopically capture the foreign material inside the basket section.

Two types of grasping tools are available, one being designed so that elastic wires forming a basket section extend in parallel to the axial direction of a sheath, and the other (so-called "Dormia" basket-type endoscopic grasping tool disclosed in Japanese Patent Kokoku Publication No. 62-42617) being designed so that pairs of elastic wires forming a basket section are each twisted in opposite directions about the central axis of a sheath.

When a foreign material of a small size is to be captured using the former type of grasping tool, the foreign material is likely to pass through a gap between adjacent elastic wires to escape to the outside of the basket section. It is not rare that the foreign material escapes in this manner.

When the latter type of grasping tool is operated such that the basket section is reciprocated in the axial direction of the sheath, the elastic wires sometimes push the foreign material aside, and hence the foreign material does not enter the basket section.

SUMMARY OF THE INVENTION

It is an object of the invention to provide a basket-type grasping tool, adapted for use in combination with an endoscope, which can easily capture a foreign material or the like into a basket section.

To attain the above-noted and other objects, the present invention provides a basket-type grasping tool adapted for use in combination with an endoscope, in which a basket section formed by at least three elastic wires bundled at both front and rear ends thereof is extractable from and retractable into a tip end of a sheath. The basket section is expanded into a basket-like shape by its own elasticity when the basket section is extracted from the tip end of the sheath, and contracted when the basket section is retracted into the tip end of the sheath.

The basket type grasping tool is characterized in that at least first axially corresponding portions of the elastic wires are twisted or bent in the same direction about a center axis of the basket section. Additionally, guide paths through which the elastic wires respectively pass are formed on an inner face of a tip-end mouth of the sheath.

The basket-type grasping tool is also characterized in that each of the elastic wires has a largely expandable middle portion, a forward portion extending forwardly from the middle portion, and a rearward portion extending rearwardly of the middle portion. At least one of the forward and rearward portions of each elastic wire is not twisted or bent about the center axis of the basket section, and the rest of the forward, middle and rearward portions of each elastic wire is partially or entirely twisted in the same direction about the center axis of the basket section.

The present disclosure relates to the subject matter contained in Japanese patent application Nos. Hei. 9-244905 (filed on Sep. 10, 1997) and 9-265707 (filed on Sep. 30, 1997), which are expressly incorporated herein by reference in their entireties.

DETAILED DESCRIPTION OF BASKET TYPE GRASPING TOOL

Figure 1:
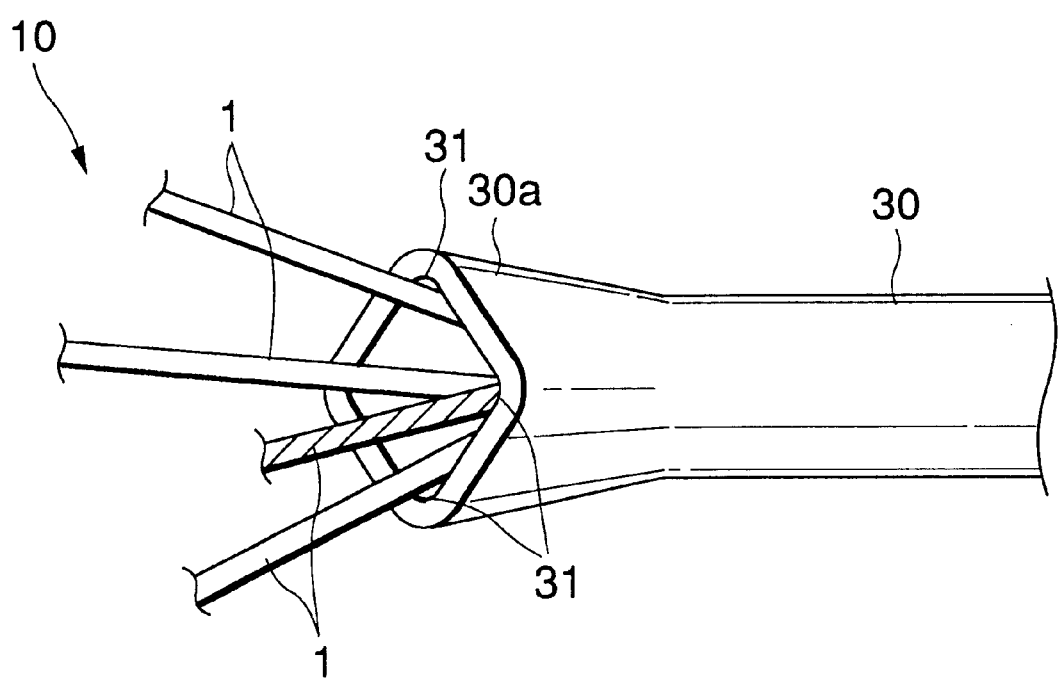
FIG. 1 is a perspective view of a tip-end mouth of a sheath of a basket-type grasping tool.
Figure 2:
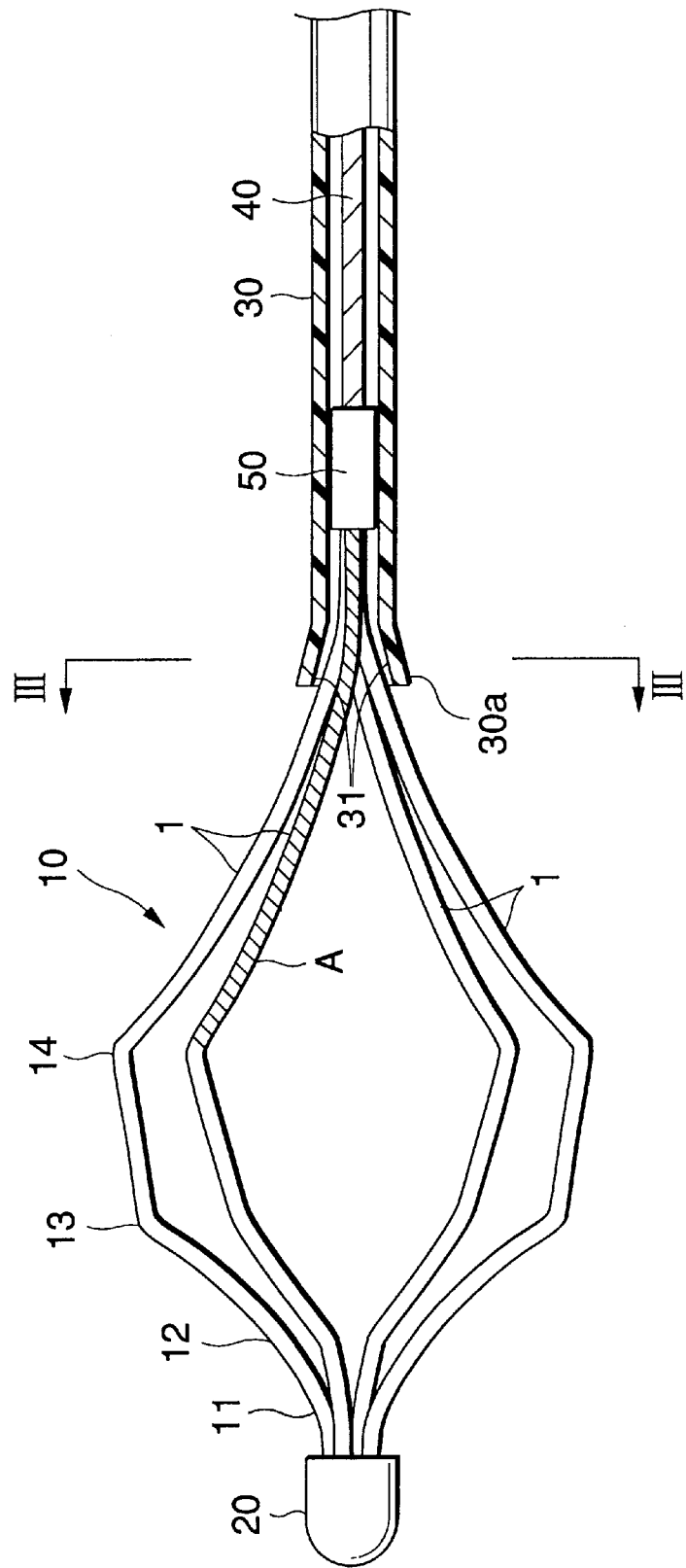
FIG. 2 is a side section view of a tip end portion in a state in which a basket section of the basket-type grasping tool is expanded.

FIGS. 1 and 2 show a tip end portion of a basket-type grasping tool. Four elastic wires 1, each of which is made, for example, of a stranded wire or solid wire of stainless steel, are bent into the same shape and then bundled at both the front and rear ends, thereby forming a basket section 10 that is expanded into a basket-like shape.

The tip ends of the four elastic wires 1 are inserted into a short tip-end bundling pipe 20 and fixed thereto by silver soldering or the like. The end face of the tip-end bundling pipe 20 is rounded into a smooth hemispherical shape.

The basal ends of the four elastic wires 1 are inserted into a rear-end bundling pipe 50 and fixed thereto by silver soldering or the like. An operating wire 40, which is made, for example, of a stranded wire of stainless steel, is inserted into the rear-end bundling pipe 50 from the opposite end, and fixed thereto by silver soldering or the like. Consequently, the four elastic wires 1 are coupled to the operating wire 40 via the rear-end bundling pipe 50.

The operating wire 40 is passed through a sheath 30 made, for example, of polytetrafluoroethylene resin, so as to be reciprocable in the axial direction. The operating wire 40 is reciprocated by an operating unit (not shown) which is coupled to the basal end of the sheath 30.

The rear-end bundling pipe 50 has an outer diameter which allows the pipe 50 to be reciprocable within the sheath 30. The basket section 10 formed by the four elastic wires 1 is extractable from and retractable into the tip end of the sheath 30 by reciprocating the operating wire 40 in the axial direction. The basket section 10 is contracted by retracting the basket section into the tip end of the sheath 30, and, when the basket section is extracted from the tip end of the sheath 30, the basket section is expanded into the original basket-like shape by its elasticity.

Each of the elastic wires 1 is bent at four bent places 11, 12, 13, and 14. The rearmost bent place 14 is located at a radially outermost position.

Figure 3:
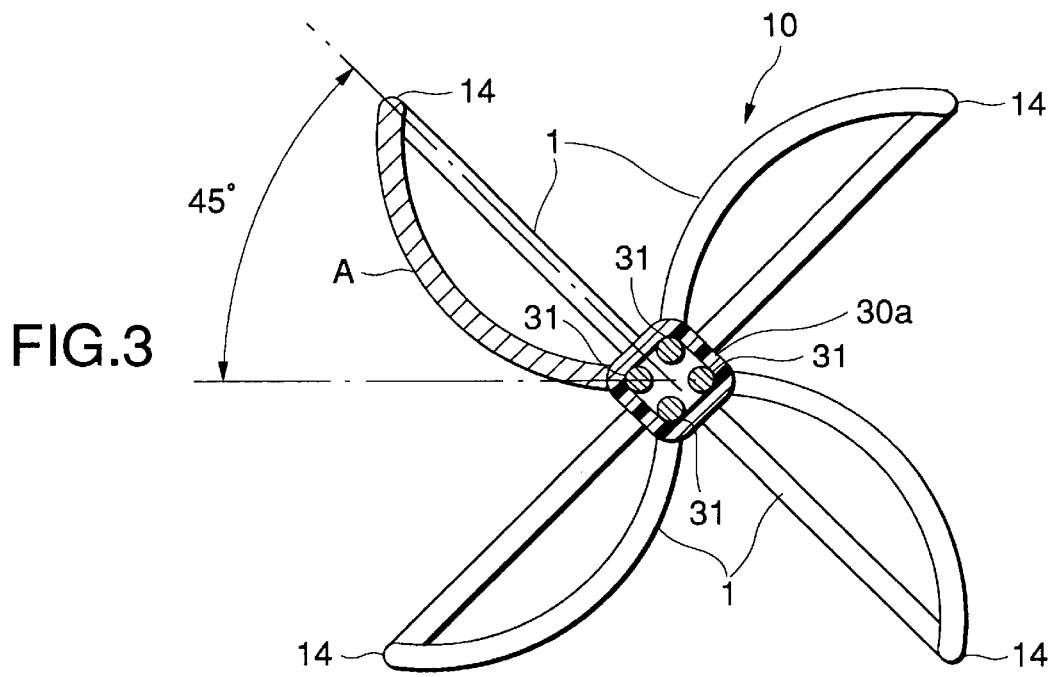
FIG. 3 is a section view of the basket-type grasping tool, taken along the line III—III of FIG. 2.

As shown in FIGS. 2 and 3, each of the four elastic wires 1 constituting the basket section 10 is constructed such that a portion of the elastic wire 1, which extends from the tip end (fixed into the short tip-end bundling pipe 20) through the bent places 11, 12, and 13 to the rearmost bent place 14, is disposed radially about the center axis of the basket section 10 without being twisted or bent with respect to the center axis of the basket section 10 (i.e., an extension line of the center axis of the tip end portion of the sheath 30).

The rest of the elastic wire 1 (the hatched portion A shown in FIGS. 2 and 3), which extends from the rearmost bent place 14 to the rear-end bundling pipe 50, is twisted or bent in the same direction about the center axis of the basket section 10 by, for example, 45°.

Although the hatched portion A is conveniently shown on only one of the elastic wires, all the four elastic wires 1 have the same portion twisted or bent about the center axis of the basket section 10 in the same rotation direction and by the same degree.

The tip end portion of the sheath 30 is expanded in a tapered manner. As shown in FIG. 3, a section of the mouth 30a perpendicular to the axis has a substantially square shape. As a result, the four elastic wires 1 pass along the four corner portions 31 of the inner face of the tip-end mouth 30a, respectively. That is, the corner portions 31 serve as elastic wire guide-paths for guiding the respective elastic wires 1 therealong.

Figure 4:
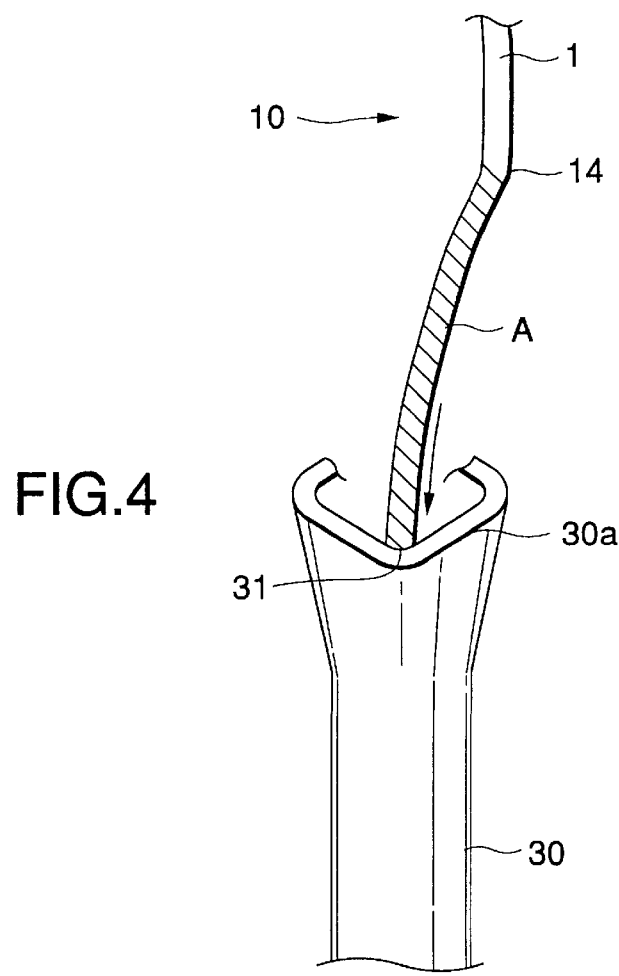
FIG. 4 is a partial perspective view illustrating the operation of an elastic wire in the basket-type grasping tool.
Figure 5:
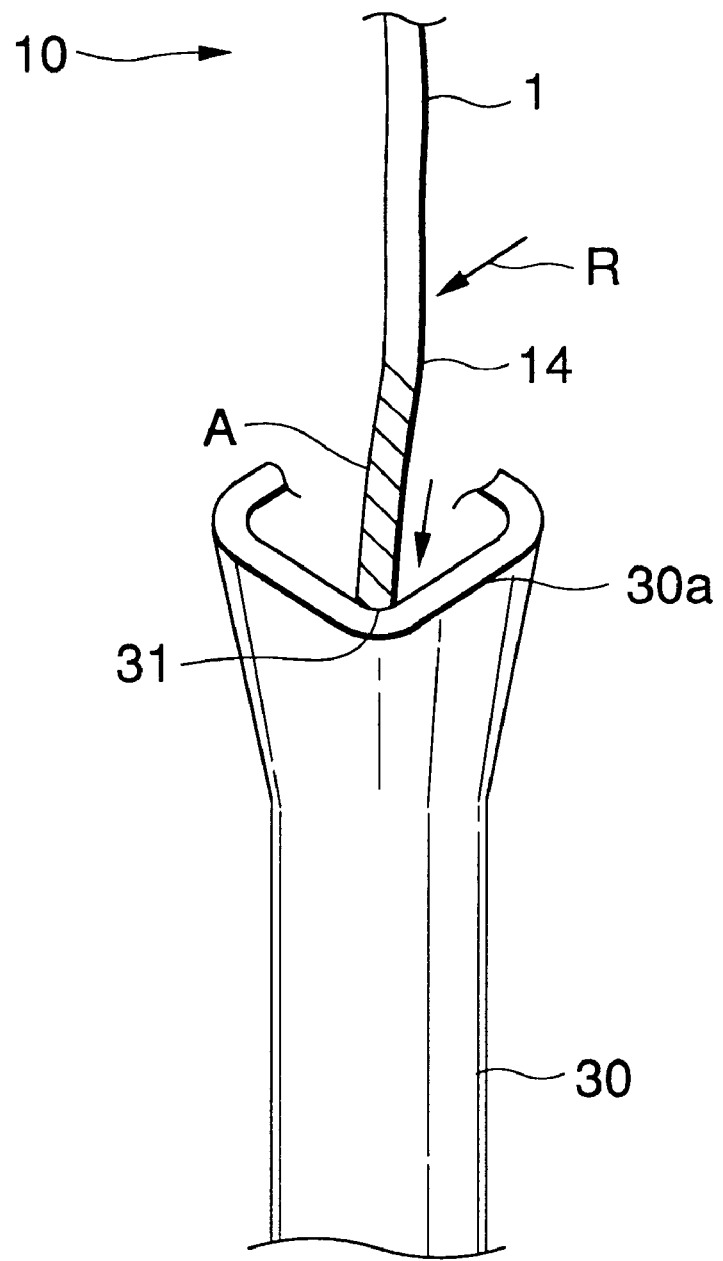
FIG. 5 is a partial perspective view illustrating the operation of the elastic wire in the basket-type grasping tool.

When the twisted portion A of each of the elastic wires 1 is pulled into the sheath 30 along the corresponding elastic wire guide path 31 as shown in FIGS. 4 and 5, the elastic wire 1 rotates about the center axis of the basket section 10 in the direction of R (see FIG. 5).

Figure 6:
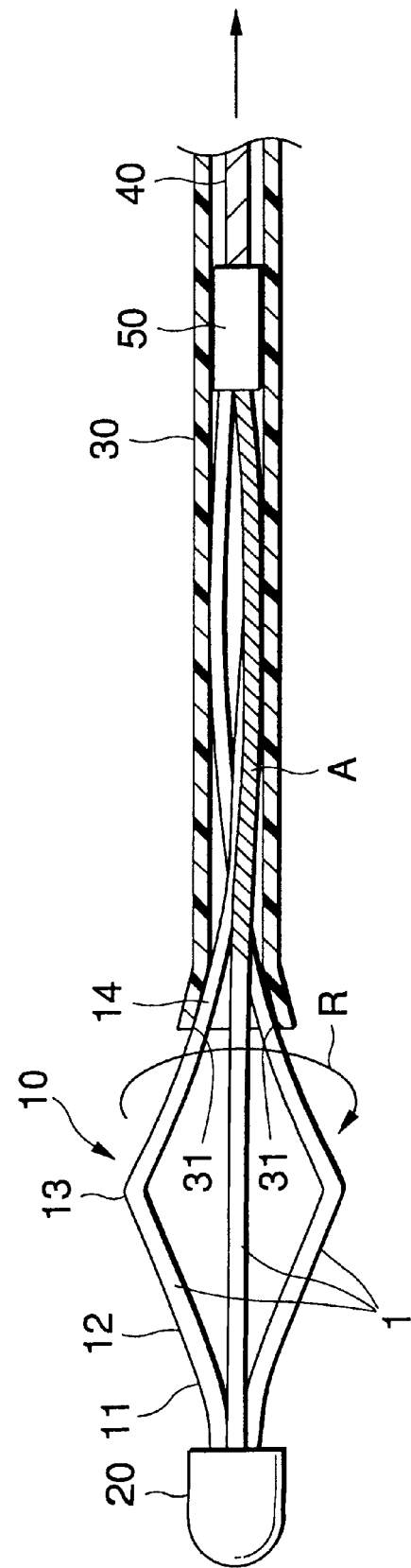
FIG. 6 is a side section view of the tip end portion in a state in which the basket section is half contracted.

In the state shown in FIG. 2, the basket section 10 is protruded from the tip end of the sheath 30 and expanded into a basket-like shape. When the operating wire 40 is pulled toward the operator, the twisted portions A of the elastic wires 1 pass the respective elastic wire guide paths 31 of the sheath 30 until the rearmost bent places 14 reach the tip-end mouth 30a of the sheath 30, as shown in FIG. 6. The action causes the basket section 10 to be retracted into the sheath 30, while rotating about the center axis.

After the rearmost bent places 14 pass the elastic wire guide paths 31, the untwisted portions of the elastic wires 1 pass through the elastic wire guide paths 31, and hence the basket section 10 is retracted into the sheath 30 without rotating.

Figure 7:
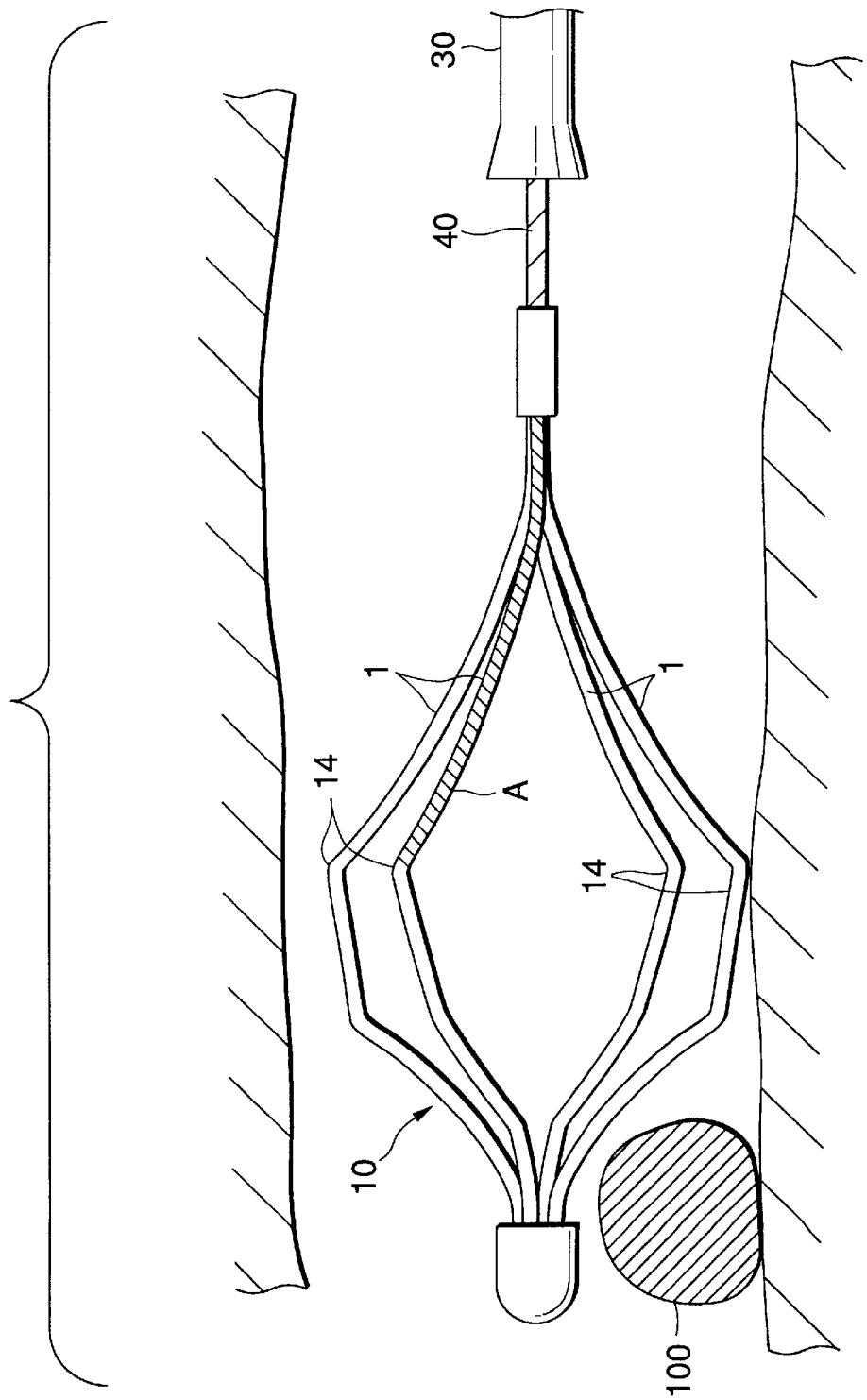
FIG. 7 is a side view showing a state in which the basket-type grasping tool is used.
Figure 8:
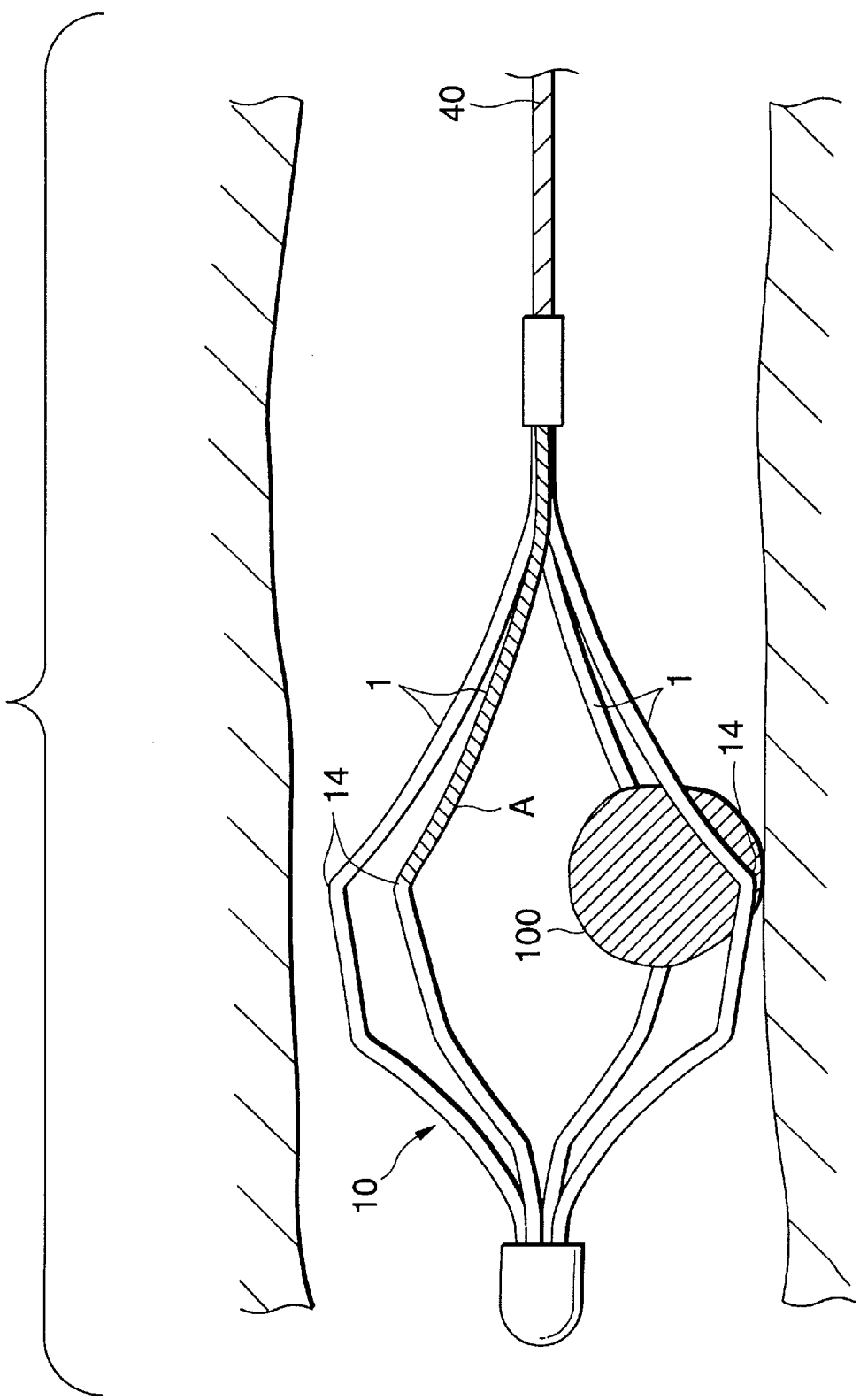
FIG. 8 is a side view showing a state in which the basket-type grasping tool is used.
Figure 9:
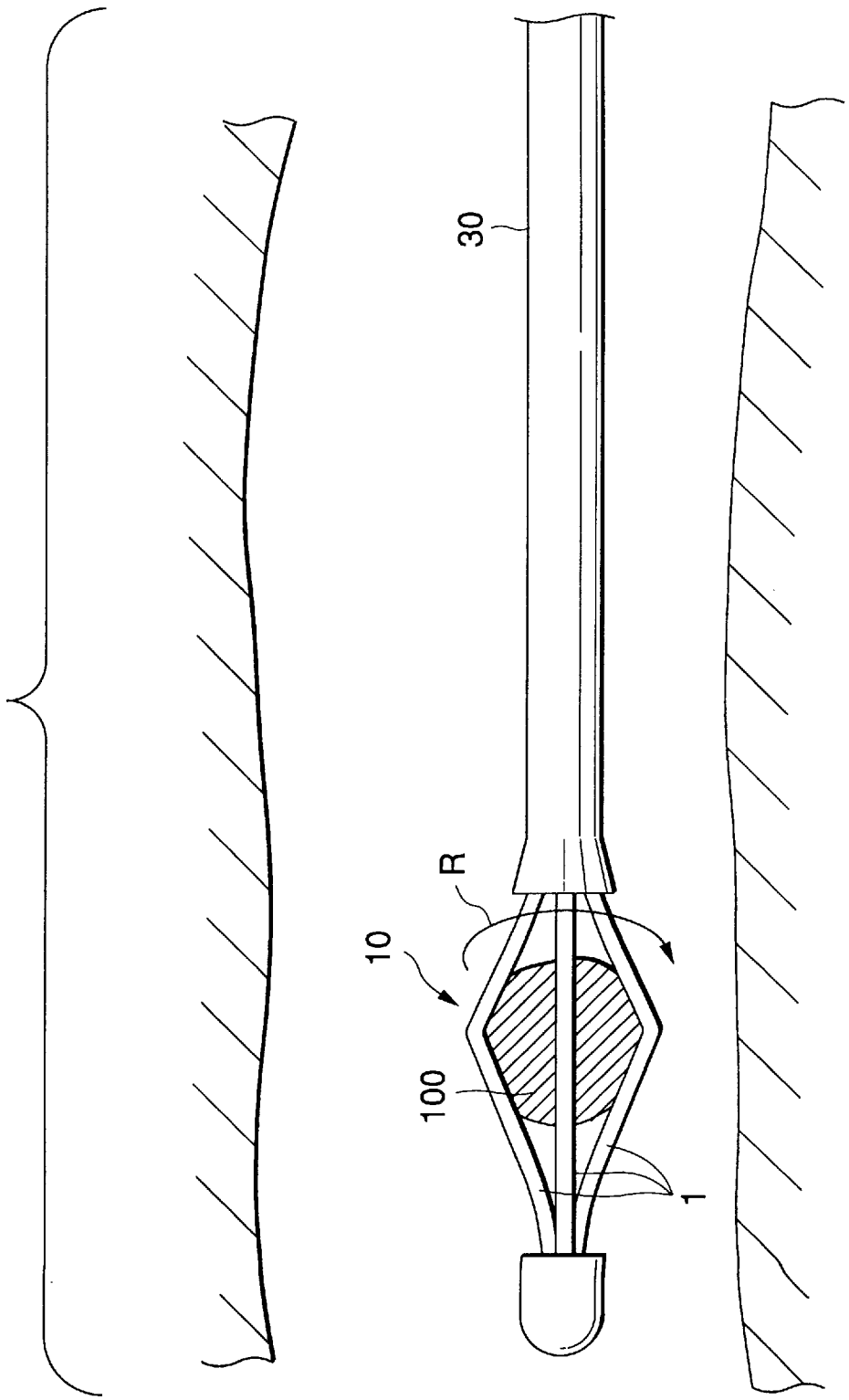
FIG. 9 is a side view showing a state in which the basket-type grasping tool is used.

FIGS. 7 to 9 show different states of the basket-type grasping tool during use. As shown in FIG. 7, the tip end of the sheath 30 first passes through a treatment tool insertion channel of an endoscope (not shown), and is then directed toward a foreign material 100 location within the body cavity. The operating wire 40 is then pushed forwardly so that the basket section 10 is pressed against the foreign material 100.

Since the forward portions of the elastic wires 1 up to the rearmost bent places 14 are not twisted or bent, the foreign material 100 easily enters into the basket section 10 through a gap between adjacent elastic wires 1 as shown in FIG. 8.

Thereafter, the sheath 30 is pushed in a forward direction, while moving the basket section 10 as little as possible. As shown in FIG. 9, the basket section 10 is contracted while rotating about the center axis, thereby attaining a state in which the foreign material 100 is tightened by the four elastic wires 1.

During this operation, if the basket section 10 does not rotate, the foreign material 100 tends to escape through a gap between adjacent elastic wires 1. However, the contraction of the basket section 10 together with the rotation thereof facilitates the catching of the foreign material 100 by the elastic wires 1, so that the foreign material 100 is securely held in the basket section 10.

The rotation angle of the basket section 10 (i.e., the twist angle of the elastic wires 1 about the center axis of the basket section 10) is 45°. In accordance with the intended purpose and the like, the rotation angle may be set to have an appropriate value in the range of about 15° to 90°.

Figure 10:
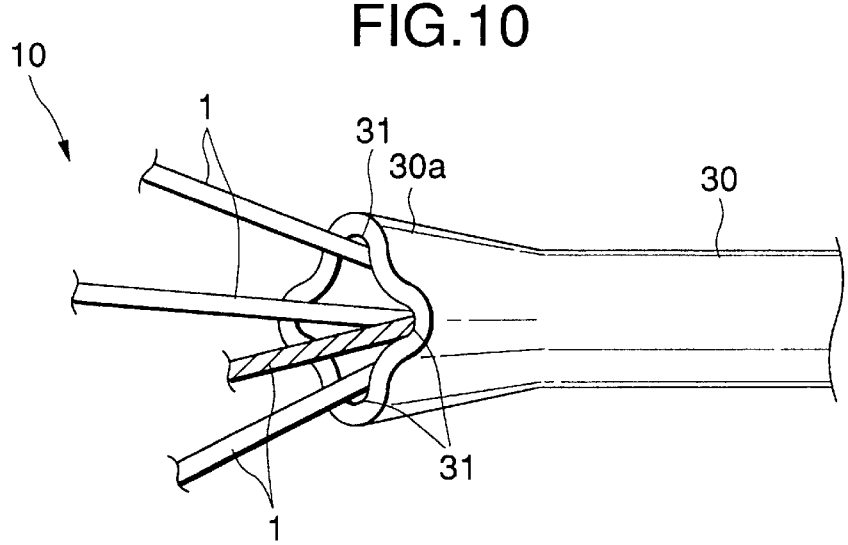
FIG. 10 is a perspective view of a tip-end mouth of a sheath of another basket-type grasping tool.

The elastic wire guide paths 31 can be defined by forming the tip-end mouth 30a of the sheath 30 into a polygonal shape corresponding to the number of elastic wires 1. As shown in FIG. 10, the tip-end mouth 30a of the sheath 30 may be formed into a star shape or the like having projections equal to the number of elastic wires 1, and grooves formed by the inner faces of the projections may constitute the elastic wire guide paths 31.

Figure 11:
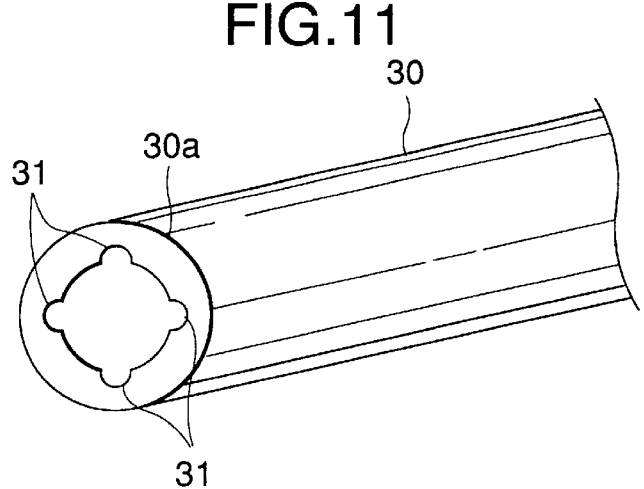
FIG. 11 is a perspective view of a tip-end mouth of a sheath of yet another basket-type grasping tool.

As shown in FIG. 11, grooves, the number of which corresponds to that of the elastic wires 1, may be formed in the tip-end mouth 30a of the sheath 30 at equal intervals, and the grooves may constitute the elastic wire guide paths 31.

Figure 12:
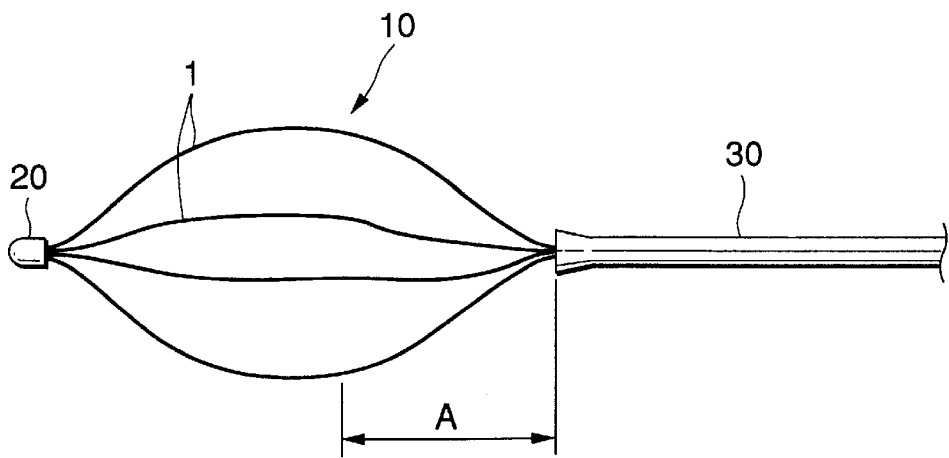
FIG. 12 is a side view of a tip end portion in a state in which a basket section of still another basket-type grasping tool is expanded.

FIG. 12 shows another basket-type grasping tool for use in combination with an endoscope. This grasping tool has a basket section 10 formed by bending each of the four elastic wires 1 so as to form a smooth curve.

Similarly to the grasping tool shown in FIG. 1, the elastic wires 1 are not twisted or bent in the most expanded and preceding portions of the basket section 10. In the range extending from slightly behind the most expanded portion of the basket section 10, to the rear end portion of the basket section 10, the elastic wires 1 are twisted or bent about the center axis of the basket section 10 in the same direction and by the same degree. As a result, the same effect can be expected as that of the grasping tool shown in FIG. 1.

Figure 13:
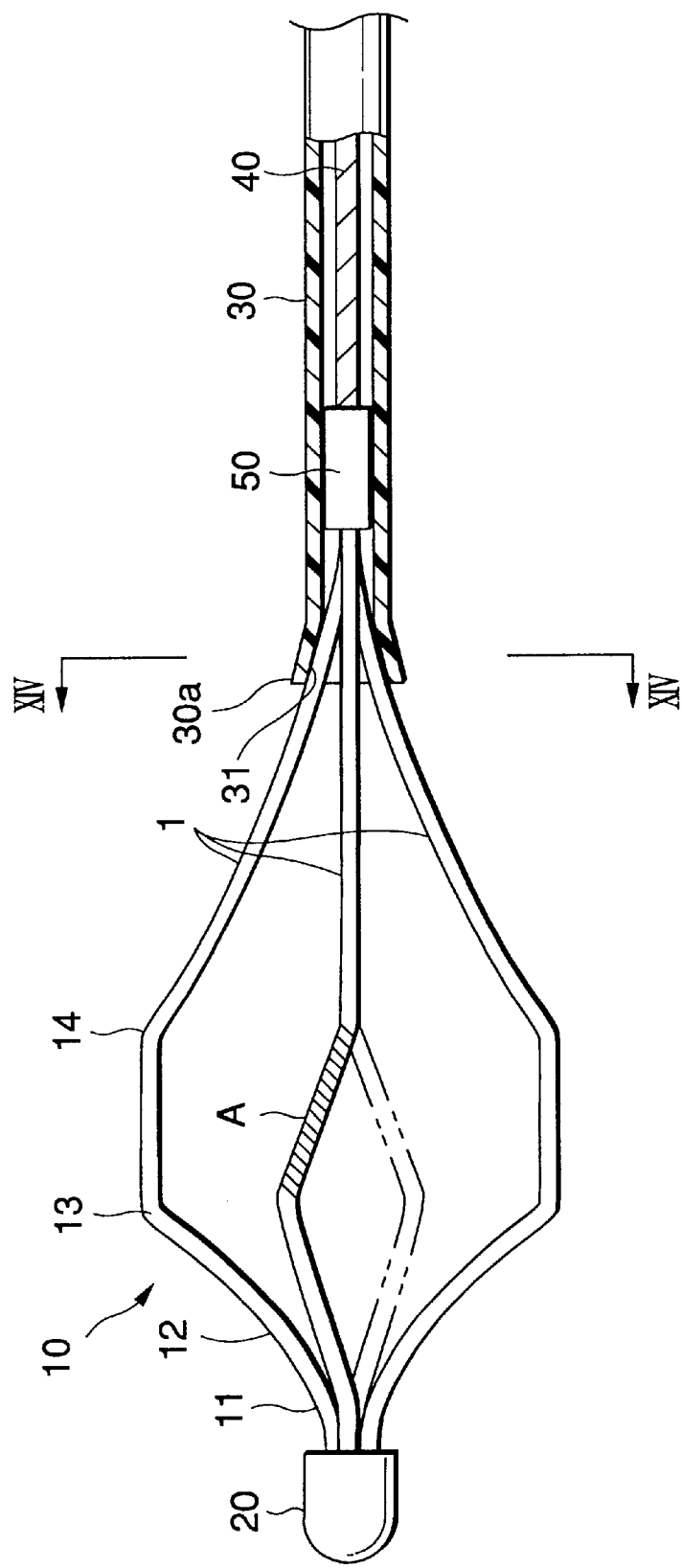
FIG. 13 is a side section view of a tip end portion in a state in which a basket section of yet another basket-type grasping tool is expanded.

FIG. 13 shows another basket-type grasping tool. Similarly to the grasping tool shown in FIG. 1, each of the four elastic wires 1 is bent at the four bent places 11, 12, 13, and 14 to form the basket section 10.

Figure 14:
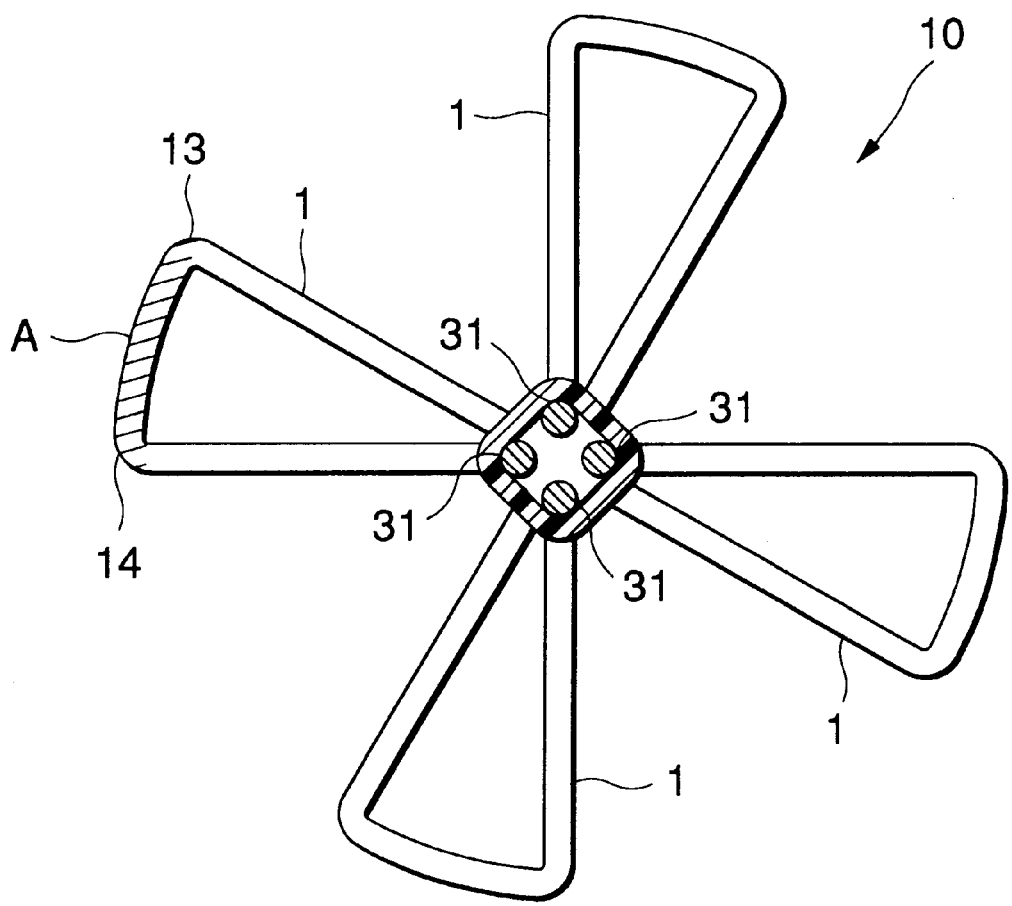
FIG. 14 is a section view taken along the line XIV—XIV of FIG. 13.

As best shown in FIG. 14, which is a section view taken along the line XIV—XIV in FIG. 13, each of the elastic wires 1 is twisted or bent about the center axis of the basket section 10 in the same direction and by the same degree only in range A, which extends from a middle portion (or a third bent place 13) of the basket section 10 to the fourth bent place 14. The other range of each of the elastic wires 1 is not twisted or bent with respect to the center axis of the basket section 10.

Figure 15:
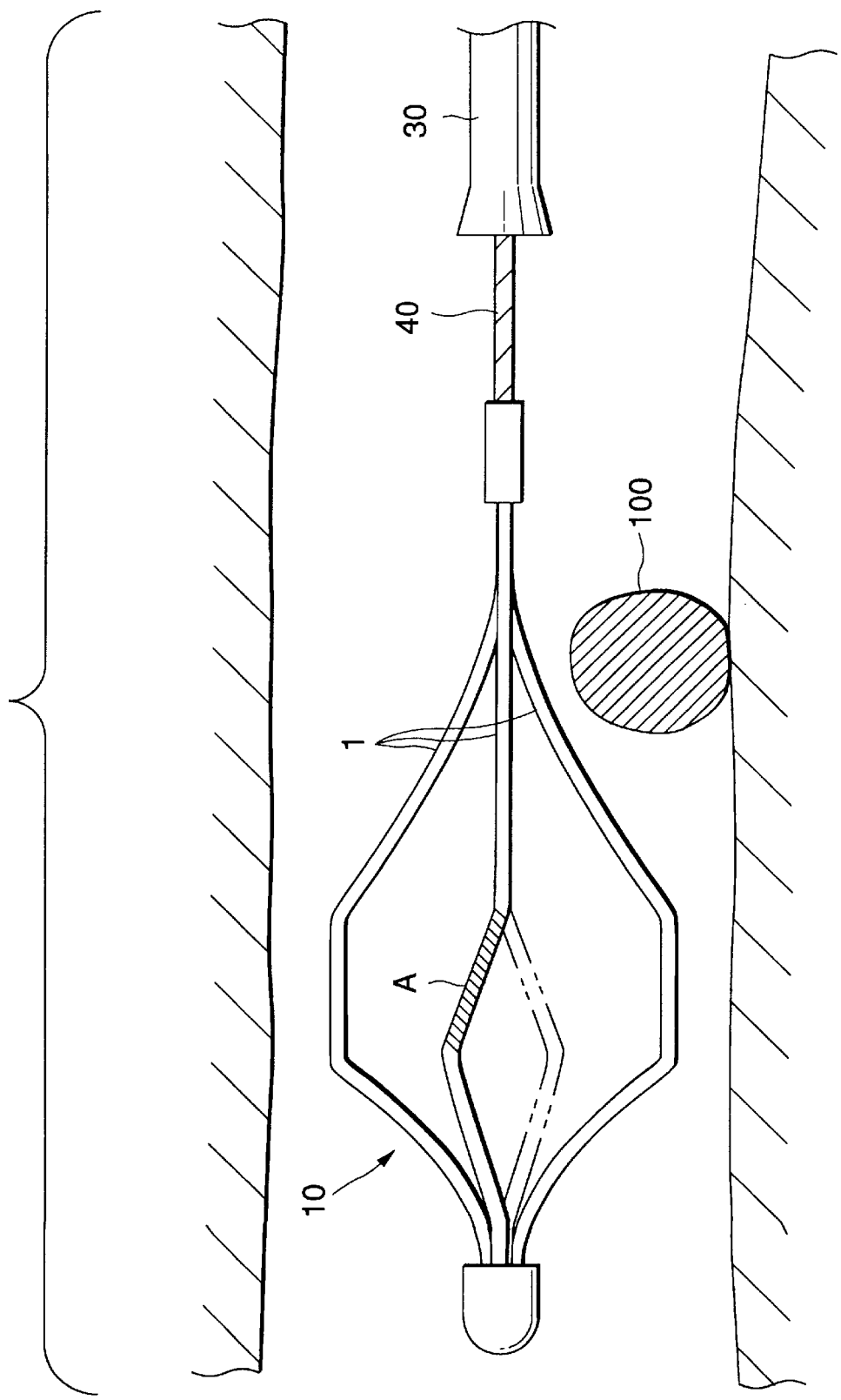
FIG. 15 is a side view showing a state in which the basket-type grasping tool shown in FIG. 13 is used.
Figure 16:
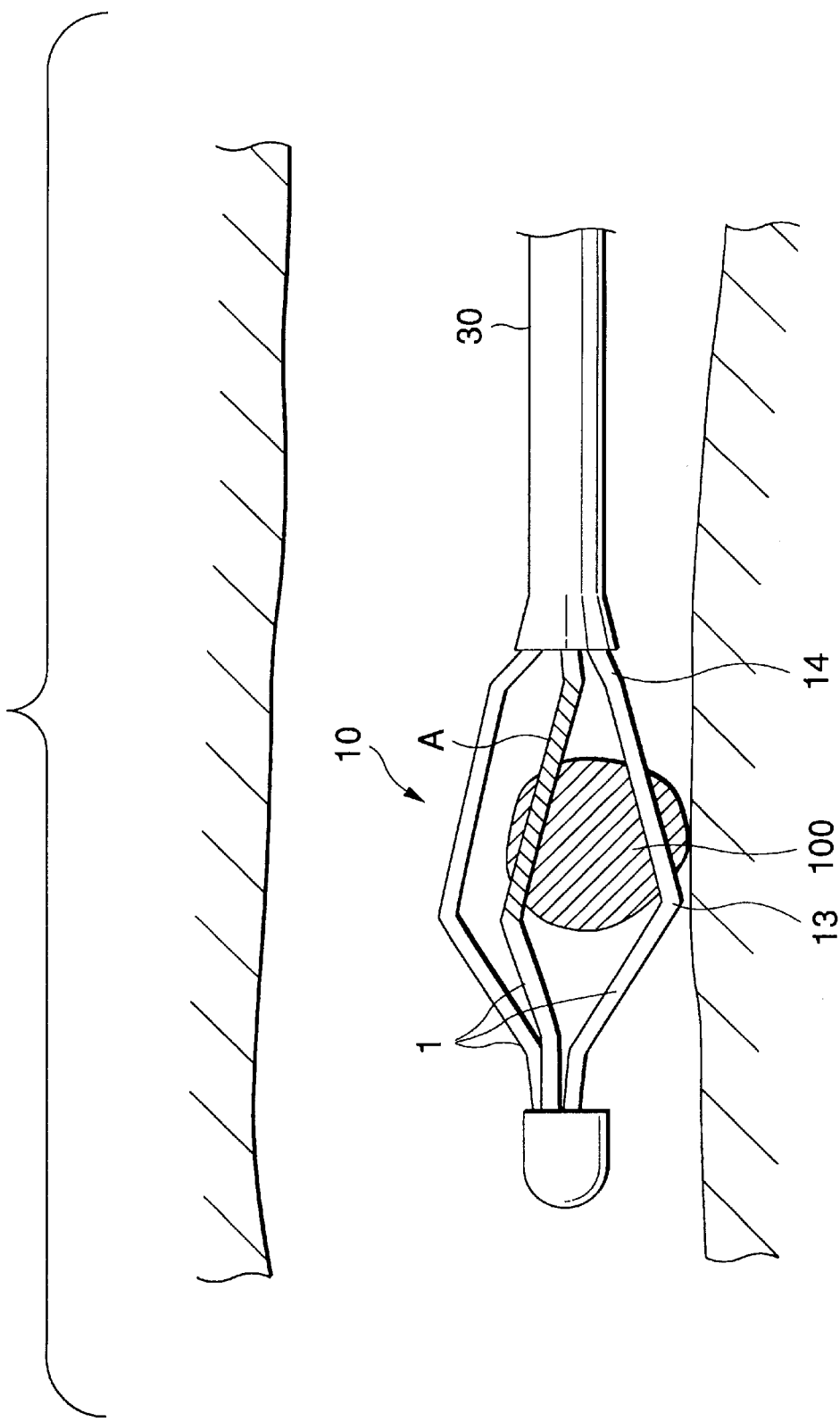
FIG. 16 is a side view showing a state in which the basket-type grasping tool shown in FIG. 13 is used.

As shown in FIG. 15, the basket section 10 is first advanced beyond the foreign material 100. The basket section 10 is then retracted toward the operator, whereby, as shown in FIG. 16, the foreign material 100 can be captured in the basket section 10 without rotating of the basket section 10.

Figure 17:
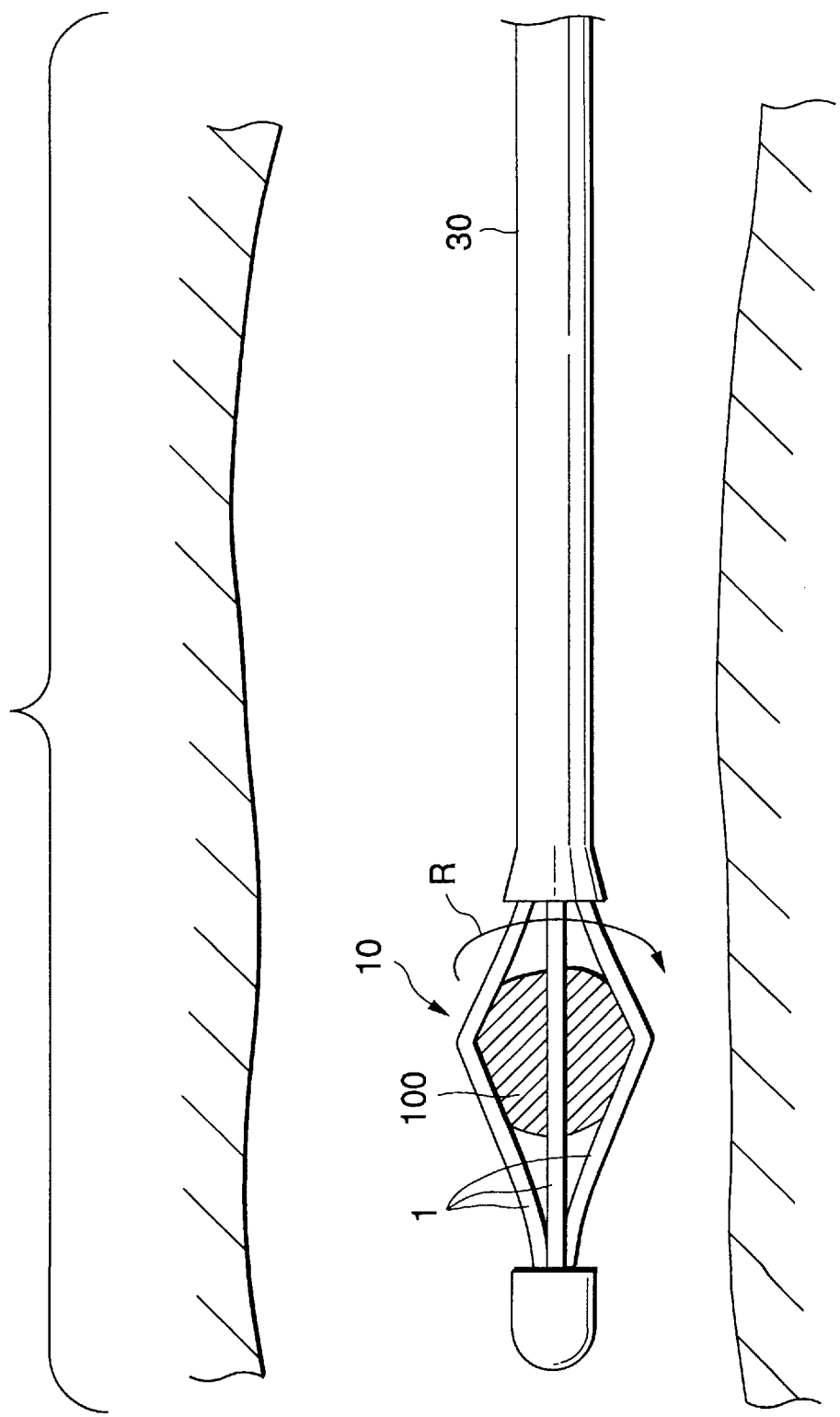
FIG. 17 is a side view showing a state in which the basket-type grasping tool shown in FIG. 13 is used.

When the basket section 10 is further retracted into the sheath 30, the twisted portions A of the elastic wires 1 pass through the elastic wire guide paths 31 formed in the tip-end mouth 30a of the sheath 30. Hence the elastic wires 1 more tightly grasp the foreign material 100 while the basket section 10 rotates about the center axis. As a result, the foreign material 100 can be securely held in the basket section 10 as shown in FIG. 17.

As described above, at least one of forward and rearward portions of each elastic wire 1, which respectively extend forwardly of and rearwardly of the largely expandable middle portion and which are not twisted or bent with respect to the center axis of basket section 10, can facilitate the capturing of the foreign material 100 into the basket section 10. The twisted or bent portion A, which is provided at least partially in each elastic wire 1 and which is twisted or bent about the center axis of the basket section 10 in the same direction, cooperates with the tip-end mouth 30a of the sheath 30 to cause the basket section 10 to rotate when the foreign material 100 is to be tightened by the basket section 10. If the elastic wire guide paths 31 are formed in the tip-end mouth 30a of the sheath 30, the twisted portions of the elastic wires 1 in combination with the guide paths 31 cause the basket section 10 to rotate in a more positive manner. Therefore, the foreign material 100 can be securely held so as not to escape from the basket section 10.

Figure 18:
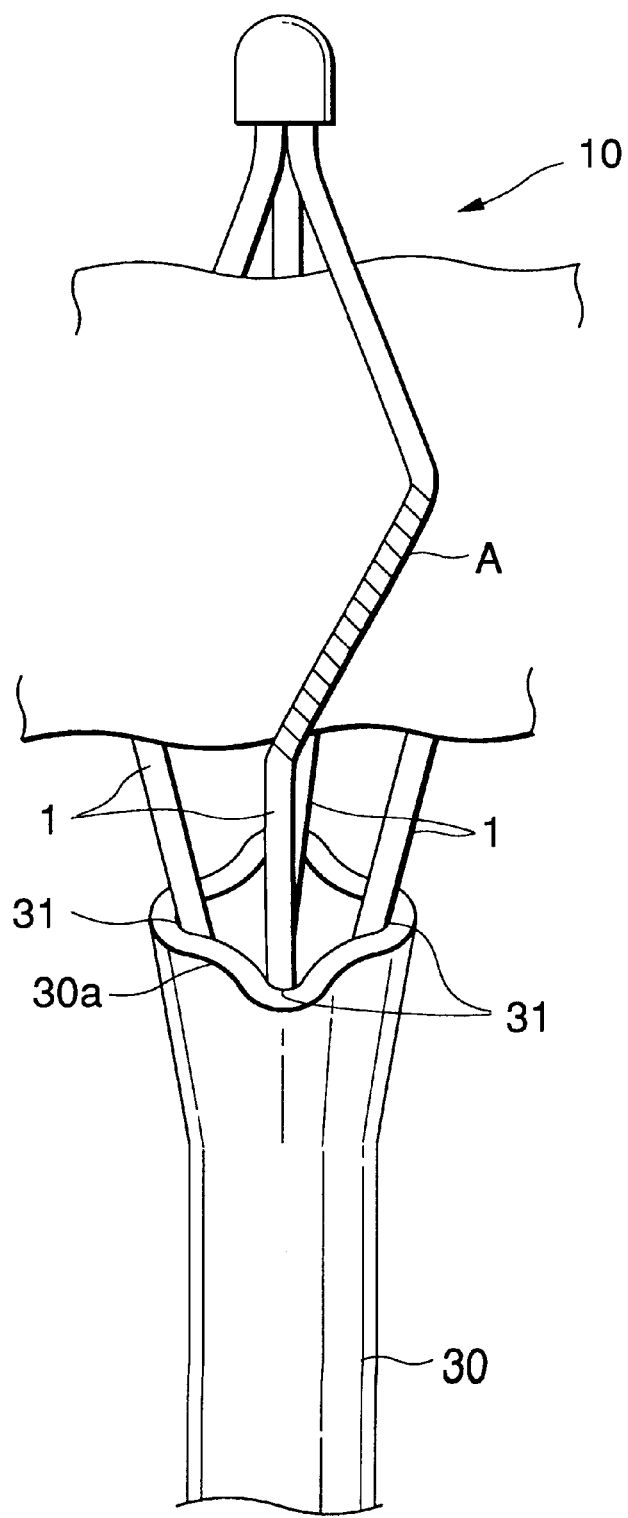
FIG. 18 is a perspective view illustrating the manner of rotation of a basket section.
Figure 19:
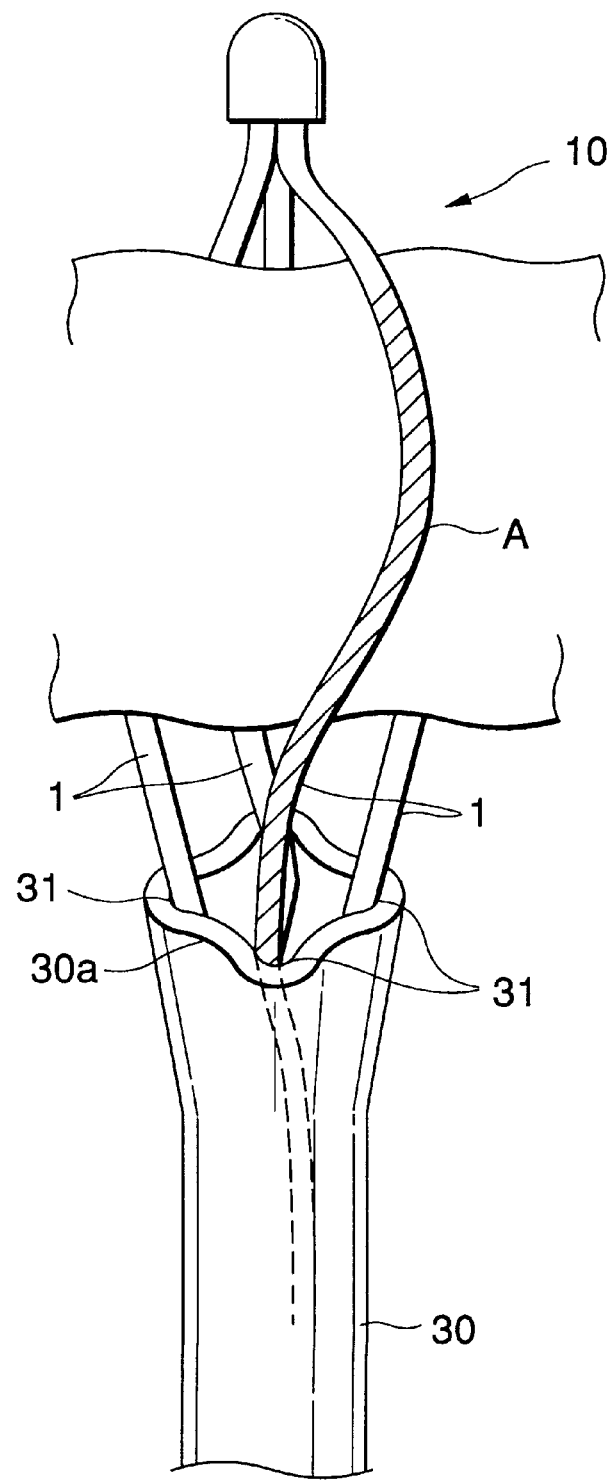
FIG. 19 is a perspective view illustrating the manner of rotation of a basket section.

The rotation of the basket section 10 can be arbitrarily set, depending on the formation of the twisted portions A of the elastic wires 1. As shown in FIG. 18, for example, the twisted or bending portions A may be formed by twisting the middle portions of the elastic wires 1 in one direction. In this case, the basket section 10 rotates in one direction, only when the twisted or bent portions A pass through the elastic wire guide paths 31. Alternatively, the twisted or bent portion A of the elastic wire 1 may be bent in opposite directions. That is, as shown in FIG. 19, the twisted or bent portion A of the elastic wire 1 is first bent in the rightward direction and then bent in the leftward direction such that the bent portion A presents a curved contour to smoothly change the twisting or bending directions. In this case, the rotating direction of the basket section 10 is gently changed from the leftward to the rightward.

Although the basket section 10 shown in the drawing has four elastic wires 1, the number of elastic wires 1 constituting the basket section 10 may be any number not smaller than three.

What is claimed is:

1. A basket-type grasping tool adapted for use in combination with an endoscope, wherein:

a basket section formed by at least three elastic wires bundled at both of front and rear ends thereof being extractable from and retractable into a tip end of a sheath so that said basket section is expanded into a basket-like shape by the elasticity of said basket section when said basket section is extracted from said tip end of said sheath, and contracted when said basket section is retracted into said tip end of said sheath, said tip end of said sheath having a center axis, and said basket section having a center axis which is an extension of said center axis of said tip end;

at least first axially corresponding portions of said elastic wires being bent about said center axis of said basket section in the same direction; and guide paths through which said elastic wires respectively pass being formed on an inner face of a tip-end mouth of said sheath.

2. A basket-type grasping tool according to claim 1, wherein said tip-end mouth of said sheath has a polygonal section shape, and corner portions of said polygonal section shape serve as said guide paths.

3. A basket-type grasping tool according to claim 1, wherein a plurality of grooves are formed in an inner peripheral face of said tip-end mouth of said sheath, and said grooves serve as said guide paths.

4. A basket-type grasping tool according to claim 1, wherein:

each of said elastic wires has a largely expandable middle portion, a forward portion extending forwardly from said middle portion, and a rearward portion extending rearwardly of said middle portion;

at least one of said forward and rearward portions of said each elastic wire is not bent about said center axis of said basket section;

the rest of said forward, middle and rearward portions of said each elastic wire is partially or entirely bent about said center axis of said basket section in the same direction.

5. A basket-type grasping tool according to claim 4, wherein said rearward portion is bent about said center axis of said basket section in the same direction.

6. A basket-type grasping tool according to claim 4, wherein said middle portion is bent about said center axis of said basket section in the same direction.

7. A basket-type grasping tool according to claim 1, wherein each of said elastic wires forming said basket section is bent at a plurality of places.

8. A basket-type grasping tool according to claim 1, wherein each of said elastic wires forming said basket section is bent to present a smooth curve.

9. A basket-type grasping tool according to claim 1, wherein said elastic wires have second axially corresponding portions which are not bent about said center axis of said basket section and which are continuous with respective first axially corresponding portions.

10. A basket-type grasping tool adapted for use in combination with an endoscope, wherein:

a basket section formed by at least three elastic wires bundled at both of front and rear ends thereof being extractable from and retractable into a tip end of a sheath so that said basket section is expanded into a basket-like shape by the elasticity of said basket section when said basket section is extracted from said tip end of said sheath, and contracted when said basket section is retracted into said tip end of said sheath, said tip end of said sheath having a center axis, and said basket section having a center axis which is an extension of said center axis of said tip end;

each of said elastic wires having a largely expandable middle portion, a forward portion extending forwardly from said middle portion, and a rearward portion extending rearwardly of said middle portion;

at least one of said forward and rearward portions of said each elastic wire not being bent about said center axis of said basket section; and the rest of said forward, middle and rearward portions of said each elastic wire being partially or entirely bent about said center axis of said basket section in the same direction.

11. A basket-type grasping tool according to claim 10, wherein guide paths through which said elastic wires respectively pass are formed on an inner face of a tip-end mouth of said sheath.

12. A basket-type grasping tool according to claim 10, wherein said rearward portion is bent about said center axis of said basket section in the same direction.

13. A basket-type grasping tool according to claim 10, wherein said middle portion is bent about said center axis of said basket section in the same direction.

14. A basket-type grasping tool according to claim 10, wherein each of said elastic wires forming said basket section is bent at a plurality of places.

15. A basket-type grasping tool according to claim 10, wherein each of said elastic wires forming said basket section is bent to present a smooth curve.

* * * * *